United States Patent [19]

Apitz et al.

[11] Patent Number: 5,316,950
[45] Date of Patent: May 31, 1994

[54] METHOD FOR QUANTITATIVE CALIBRATION OF IN SITU OPTICAL CHEMICAL MEASUREMENTS IN SOILS USING SOIL CLASS AND CHARACTERISTICS

[75] Inventors: Sabine E. Apitz, San Diego; Stephen H. Lieberman, La Mesa, both of Calif.

[73] Assignee: The United States of America as represented by the Secretary of the Navy, Washington, D.C.

[21] Appl. No.: 10,024

[22] Filed: Jan. 21, 1993

[51] Int. Cl.$^5$ ............... G01N 33/24; G01N 21/64
[52] U.S. Cl. ............... 436/28; 73/84; 422/82.07; 422/82.08
[58] Field of Search ............... 436/28; 422/82.06-82.08; 73/84

[56] References Cited

U.S. PATENT DOCUMENTS

| | | |
|---|---|---|
| 3,906,781 | 9/1975 | Vlasblom. |
| 4,084,248 | 4/1978 | Scott. |
| 4,414,638 | 11/1983 | Talambiras. |
| 4,437,164 | 3/1984 | Branch, III. |
| 4,669,052 | 5/1987 | Bianco. |
| 4,866,644 | 9/1989 | Shenk et al.. |
| 4,975,581 | 12/1993 | Robinson et al.. |
| 5,128,882 | 7/1992 | Cooper et al.. |

OTHER PUBLICATIONS

Apitz, S. E. et al. "Remote in situ Determination of Fuel Products in Soils: Field Results and Laboratory Investigations", *Analusis*, 20, 461–474, 1992 (invited paper).

Apitz, S. E. et al. "Optimization of the Optical Characteristics of a Fiber-Optic Guided Fluorescence Technique for the in situ Evaluation of Fuels in Soils," in *SPIE Proceedings* vol. 1637, Environmental Process and Treatment Technologies, T. Vo-Dinh, ed., 241–254, 1992.

Apitz, S. E. et al. "The Fluorescent Response of Fuels in Soils: Insights into Fuel-Soil Interactions," in International Symposium on Environmental Sensing, EOS/SPIE Proceedings vol. 1716, 1992 (in press).

Barcelona, M. J. et al. *Practical Guide for Ground-water Sampling*, EPA Rep. EPA/600/S2-85/104, 94 pp. EPA, Washington, DC, 1985.

Chudyk, W. A. "Field Screening of Hazardous Waste Sites," *Env. Sci. and Tech.*, 23, 504–505, 1989.

Cooper, S. S. et al. *Development of a Computerized Penetrometer System for Hazardous Waste Site Soils Investigations*, Rept. No. AMXTH-TR-TE-882452, U.S. Army Toxic and Hazardous Materials Agency, Aberdeen Proving Ground, MD, 1988.

(List continued on next page.)

*Primary Examiner*—Jill A. Johnston
*Attorney, Agent, or Firm*—Harvey Fendelman; Thomas Glenn Keough

[57] ABSTRACT

A method assures the quantitative or semiquantitative assessment of analytes in soils by in situ optical methods. A determination is made of the optical chemical response factors for chemicals of interest which are added in known amounts to discrete soil matrices (types) and conditions (moisture content) under controlled laboratory conditions to provide predetermined reference signals. A combination probe is provided with an optical chemical sensing device that produces chemical concentration signals representative of the concentration of a chemical of interest in a soil sample and further is provided with a strain gauge sensing device that produces strain gauge signals representative of soil type and optionally, condition of the soil sample. The combination probe is inserted into the soil sample and the optical chemical sensing device produces the chemical concentration signals and the optical strain gauge sensing device, simultaneously and in parallel, produces the optical strain gauge signals. The optical chemical concentration signals and strain gauge signals are fed to a processor where they are compared to the predetermined reference signals to arrive at an in situ quantification of chemicals of interest in the soil sample.

2 Claims, 1 Drawing Sheet

OTHER PUBLICATIONS

Freeze, R. A. & Cherry, J. A. *Groundwater*, 604 pp. Prentice-Hall, Inc., Englewood Cliffs, N.J., 1979, Textbook (copy not provided).

Hirschfeld, T., et al. "The Feasibility of Using Fiber Optics for Monitoring Groundwater Contaminants," *Optical Eng.*, 22, 527–531, 1981.

Lieberman, S. H., et al. Subsurface Screening of Petroleum Hydrocarbons in Soils via Laser Induced Fluorometry over Optical Fibers with a Cone Penetrometer System, in *International Symposium on Environmental Sensing, EOS/SPIE Proceedings*, vol. 1716, 1992 (in press).

Lieberman, S. H., et al. "Rapid, Subsurface *in situ* Screening of Petroleum Hydrocarbon Contamination Using Laser Induced Fluorescence over Optical Fibers," in *Field Screening Methods for Hazardous Wastes and Toxic Chemicals, Second International Symposium*, 57–63, 1991.

Lieberman, S. H., et al. "Fiber Optic Fluorescence Sensors for Remote Detection of Chemical Species in Seawater," in *Proceedings of the Symposium on Chemical Sensors*, 87, Electrochemical Society, Pennington, N.J., 463–473, 1987.

Milanovich, F. P., et al. "A Fiber Optic Sensor for the Continuous Monitoring of Chlorinated Hydrocarbons," in *Field Screening Methods for Hazardous Wastes and Toxic Chemicals, Second International Symposium*, 43–48, 1991.

Olsen, R. S., & Farr, J. V. "Site Characterization Using the Cone Penetrometer Test," in Proceedings of the ASCE Conference on Use of In-*Situ Testing in Geotechnical Engineering*, Amer. Soc. of Civil Eng., New York, N.Y., 1986, (copy not available, updated analogus 1988 copy provided).

Robertson, P. K., & Campanella, R. G. *Guidelines for Geotechnical Design Using the Cone Penetrometer Test and CPT with Pure Pressure Measurement*, Fourth Ed., 185 pp., Hogentogler & Co., Inc., Columbia, MD, 1989.

Seitz, W. R. "Chemical Sensors Based on Fiber Optics," *Anal. Chem.*, 56, 16A–34A, 1984.

Wolfbeis, O. S. "Fluorescence Optical Sensors in Analytical Chemistry," *Trends in Analytical Chemistry*, 4, 184–188, 1985.

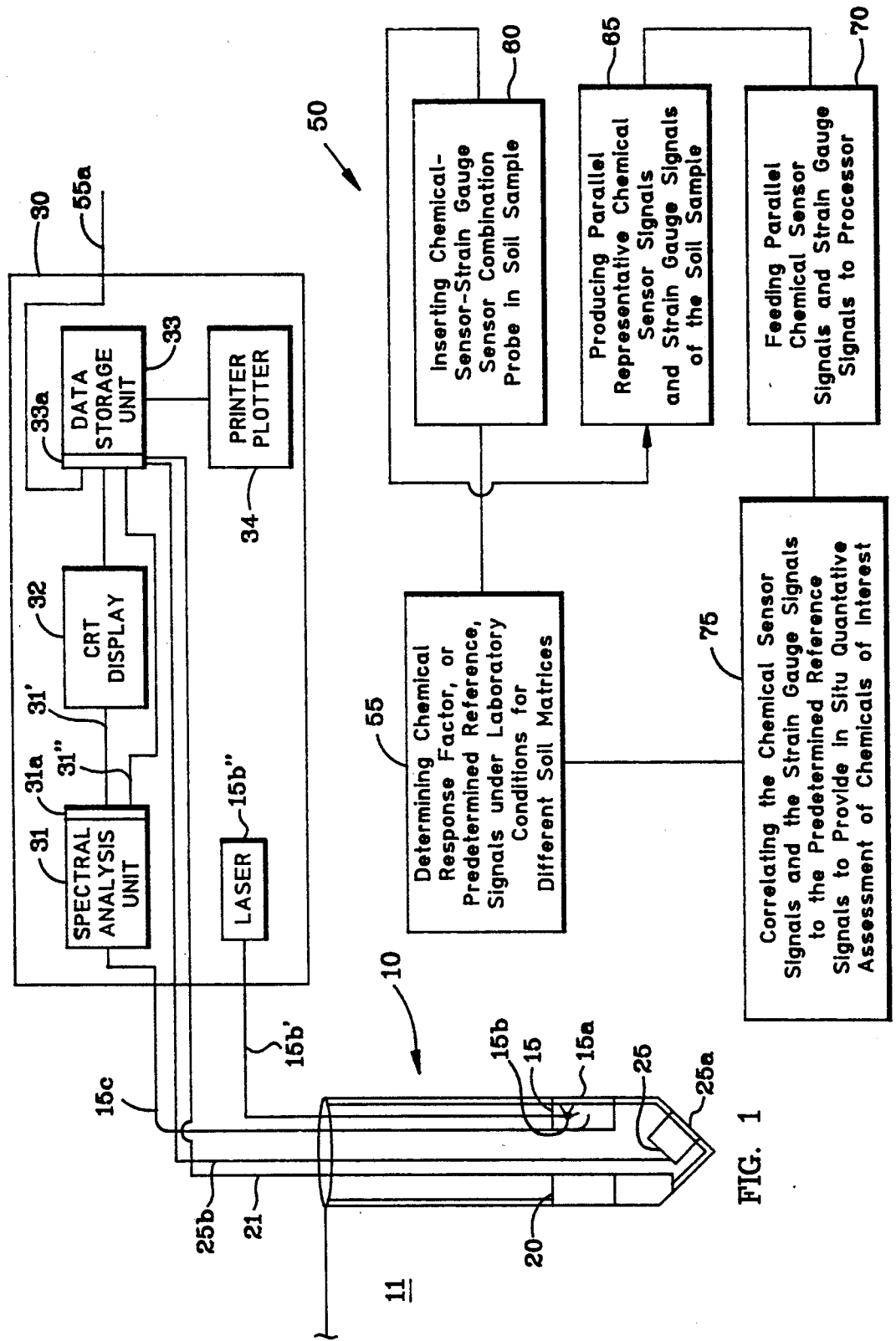

METHOD FOR QUANTITATIVE CALIBRATION OF IN SITU OPTICAL CHEMICAL MEASUREMENTS IN SOILS USING SOIL CLASS AND CHARACTERISTICS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Increasing concern with soil and groundwater contamination and governmental mandated requirements to clean up hazardous waste sites have made clear that rapid and cost effective methods for subsurface characterization of subsurface chemical contaminants are needed. Traditional methods for monitoring hazardous wastes in ground water systems have involved the collection of field samples and subsequent analysis in the laboratory, see for example, the texts by R.A. Freeze and J.A. Cherry, *Groundwater*, 604 pp., Prentice-Hall, Inc., Englewood Cliffs, N.J., 1979 and M.J. Barcelona, J.P. Gibb, J.A. Helfrich and E.E. Garske, *Practical Guide for Ground-water Sampling*, EPA Rep. EPA/600/S2-85/104, 94 pp., EPA, Washington, D.C., 1985. However, much current research has focused on the development of real-time, remote, in situ techniques to monitor both organic and inorganic pollutants.

Traditionally, samples are often collected "blind" without a priori knowledge about the exact location and extent of contaminant plumes. Zones or plumes of contamination can be completely missed, or, if pinpointed, overestimated or underestimated. For more detailed spatial information on contaminated areas, those areas must often be sampled and analyzed in an iterative manner. Such an approach can be prohibitively costly and labor-intensive. In a highly dynamic aquatic system, the delay from sampling to interpretation and remediation can severely hamper response time, or hinder contaminant containment, possibly resulting in a much larger extent and expense of cleanup.

Real-time in situ measurements, on the other hand, allow for rapid interpretation of the distribution of contaminants, through close sampling and thorough mapping of contaminated areas. The transport of contaminants in soils and/or ground water can be monitored and predicted, and cleanup operations can be efficiently planned and directed. Furthermore, remote in situ methods minimize the risk of sampling artifacts and allow for analysis in hostile environments, without exposing personnel to toxic contaminants.

One method for measuring contaminants which has been extensively discussed is the use of fiber-optic guided systems for in situ spectroscopy and chemical sensing, see the articles by T. Hirschfeld, T. Deaton, F. Milanovich and S. Klainer, entitled "The Feasibility of Using Fiber Optics for Monitoring Groundwater Contaminants," *Optical Eng.*, vol. 22, pp. 527-531, (1981); W. R. Seitz, entitled "Chemical Sensors Based on Fiber Optics," *Anal. Chem.*, vol. 56, pp. 16A-34A (1984); O. S. Wolfbeis, entitled "Fluorescence Optical Sensors in Analytical Chemistry," *Trends in Analytical Chemistry*, vol. 4, pp. 184-188 (1985); and S. H. Lieberman, S. M. Inman and E. J. Stromvall, entitled "Fiber Optic-Fluorescence Sensors for Remote Detection of Chemical Species, in Seawater," in *Proceedings of the Symposium on Chemical Sensors*, vol. 87, Electrochemical Society, Pennington, N.J., pp. 464-473 (1987); and F. P. Milanovich, P. F. Daley, K. Langry, B. W. Colston Jr., S. B. Brown and S. M. Angel, "A Fiber Optic Sensor for the Continuous Monitoring of Chlorinated Hydrocarbons," in *Field Screening Methods for Hazardous Wastes and Toxic Chemicals, Second International Symposium*, pages 43-48 (1991).

One new technology for rapid, in situ subsurface screening of hazardous waste sites is the use of a cone penetrometer system equipped with an optical chemical sensor system. Conventional cone penetrometers have been used for many years to make measurements of soil strength characteristics, see the articles by R. S. Olsen and J. V. Farr, "Site Characterization Using the Cone Penetrometer Test," in *Proceedings of the ASCE Conference on Use of In-situ Testing in Geotechnical Engineering*, American Society of Civil Engineers, New York (1986); and P. K. Robertson and R. G. Campanella, *Guidelines for Geotechnical Design Using the Cone Penetrometer Test and CPT with Pore Pressure Measurement*, Fourth Ed., 185 pp. Hogentogler & Co., Inc., Columbia, Md. (1989).

Recently, a cooperative effort with many participants has developed a prototype cone penetrometer system that has been modified to accommodate a laser induced optical fiber fluorometer for real-time, in situ measurement of chemical contaminants in soils. The prototype system has been used to demonstrate the feasibility of real-time in situ fluorescence measurements of POL (petroleum, oils, and lubricants) in soils as the probe is pushed into the ground to depths of up to 150 feet. The fiber optic system used in the prototype penetrometer has been described in the article by S.H. Lieberman, G.A. Theriault, S.S. Cooper, P.G. Mallone, R.S. Olsen and P.W. Lurk. entitled "Rapid, Subsurface in situ Screening of Petroleum Hydrocarbon Contamination Using Laser Induced Fluorescence over Optical Fibers," in *Field Screening Methods for Hazardous Wastes and Toxic Chemicals, Second International Symposium*, 57-63, 1991.

In brief, the prototype cone penetrometer system uses two silica clad silica UV/visible-transmitting optical fibers. One fiber is used to carry excitation radiation down through the center of the penetrometer probe and a second fiber collects the fluorescence generated in the soil sample and carries it back to the detector system. The two fibers are separated from the soil sample by a sapphire window mounted flush with the outside of the probe. In the prototype system excitation radiation is provided by a pulsed $N_2$ laser. A photodiode array detector coupled to a spectrograph is used to quantify the resulting fluorescence emission spectrum. While other fiber-optic guided chemical sensors are being developed for use in groundwater contaminant studies, this is the first reported direct optical detector for contaminants in soils. Unlike sensing systems which examine the contaminant levels in monitoring wells, such as referred to in W. A. Chudyk's, "Field Screening of Hazardous Waste Sites," *Env. Sci. and Tech.*, vol. 23 pages 504-505 (1989), the Lieberman et al. system allows for measurements in soils before monitoring wells are drilled, and, as a consequence is independent of the fractionation and transport problems inherent in using well samples to determine contaminant levels on and between soil particles. However, the prototype core penetrometer system does not take into account the influence of soil type and condition on the readings obtained.

Thus, a continuing need exists in the state of the art for a method providing an improved quantification of the measured optical response of chemical sensors for in situ measurement of chemical constituents in soils which is dependent on critical parameters of soil type and conditions.

SUMMARY AND OBJECTS OF THE INVENTION

The present invention is directed to providing a method for improving the calibration of the response from optical chemical sensors for in situ guantification of chemical constituents in soil. First, a determining of the optical chemical response factors is made for chemicals of interest which are added in known amounts to discrete soil matrices (types) and conditions (moisture content) under controlled laboratory conditions to provide predetermined reference signals. Next, a combination probe is provided having an optical chemical sensing device that produces chemical concentration signals representative of the concentration of a chemical of interest in a soil sample and further having a strain gauge device that produces strain gauge signals representative of soil type. The combination probe is inserted into the soil test sample so that the chemical sensing device produces the chemical concentration signals and the strain gauge device, simultaneously and in parallel, produces the strain gauge signals. This allows a feeding of the chemical concentration signals and strain gauge device signals to a common analysis unit and a comparing of the chemical concentration signals and strain gauge device signals to the predetermined reference signals to arrive at an in situ quantification of chemical constituents in the soil sample.

An object of the invention is to provide an improved quantification of the measured optical response of chemical sensors.

Another object is to provide a method for taking into account environmental controls on the response of the contaminant being sensed.

Another object is to provide a method using strain-gauge-deduced soil classification information as a means of correcting for soil matrix effects on in situ optical chemical measurements.

Another object is to provide an improved quantification of the measured optical response of chemical sensors adapted for in situ measurement of chemical constituents in soil.

Another object is to provide an improved method relying on parallel, simultaneously gathered strain gauge measurement signals and chemical response measurement signals to provide improved optical response quantification signals.

Another object is to provide soil classification information derived from strain gauge measurements that provide an index of soil type to enable an appropriate optical response factor used for calibration of the optical chemical sensor.

These and other objects of the invention will become more readily apparent from the ensuing specification and drawings when taken in conjunction with the appended claims.

BRIEF DESCRIPTION OF THE DRAWINGS

FIG. 1 is a schematic representation of a combination probe coupled to processing circuitry in accordance with this inventive concept.

FIG. 2 is a block diagram representation of the method of this inventive concept.

DESCRIPTION OF THE PREFERRED EMBODIMENT

The method of this inventive concept is to the improvement of the calibration of the response from optical chemical sensors that have been used for in situ determinations of the chemical constituents of soils. The chemical constituents of interest are most likely to be contaminants from hazardous waste sites or other locations where the environment is being threatened by objectionable chemical concentrations. These contaminants may be, yet are not limited to, the fluorescing contaminants, such as diesel fuel, jet fuel, gasoline, lubricating oils, creosote, wood processing wastes etc., for example. The improvement by the method of this inventive concept allows the calibration of response from optical chemical sensors as a function of different soil types and conditions to enable an in situ quantification of chemical constituents in soils.

In situ optical measurements in soils are highly sensitive to soil type and conditions, due to soil-influenced effective cell size, moisture effects, and other environmental effects, see the articles by S.E. Apitz, L.M. Borbridge, G.A. Theriault and S.H. Lieberman, "Remote in situ Determination of Fuel Products in Soils: Field Results and Laboratory Investigations," *Analysis,* 20,461–474, 1992 (invited paper), by S.E. Apitz, L.M. Borbridge, K. Bracchi and S.H. Lieberman, "The Fluorescent Response of Fuels in Soils: Insights into Fuel-Soil Interactions," in *International Symposium on Environmental Sensing, EOS/SPIE Proceedings, Vol.* 1716, 1992 (in press) and by S.E. Apitz, G.A. Theriault and S.H. Lieberman, "Optimization of the Optical Characteristics of a Fiber-optic Guided Fluorescence Technique for the in situ Evaluation of Fuels in Soils," in *SPIE Proceedings, Vol.* 1637, *Environmental Process and Treatment Technologies,* T. Vo-Dinh, ed., 241–254, 1992.

This invention provides a protocol for determining the magnitude and range of these effects, and provides for the inclusion of these soil characteristics in the chemical calibration algorithms or other chemical of interest determinations. In the case of the cone penetrometer test (CPT) system equipped with an optical sensor, this invention allows for the inclusion of CPT-generated soil class directly into calibration algorithms or other chemical of interest determinations. Without this soil-dependent calibration, in situ optical assessment of contaminants or naturally occurring compounds in soils will be order-of-magnitude estimates, at best. The soil types which are accommodated are sandy soil, silt, clay, etc..

Referring now to FIG. 1, the improved method of this invention relies upon the data that may be simultaneously collected from a single combination probe 10. The combination probe may be configured to have much the same appearance as the above referred to CPT but differs in its simultaneous dual data function which is provided by an optical chemical sensor 15 and a strain gauge sensor 20 appropriately disposed within the confines of the probe, though not necessarily as depicted, to provide responsive readings. The probe is driven into the ground so as to permit independent determinations of soil type (or classification) in parallel with optical chemical measurements that are made using the same probe. In keeping with the method of this inventive concept, the integration of soil class and characteristics with optical response of analytes in soils is essential for the quantitative in situ evaluation of contaminants. For example, it has been demonstrated that the fluorescent response of diesel fuel marine varies more than an order of magnitude in different soil types. This is primarily the result of soil type controlling the amount of analyte visible to an optical detector. Soil type will most likely affect the intensity of optical response for all contaminants in soils. Thus, soil type must be taken into account in calibration algorithms for quantitative or semi-quantitative in situ optical evaluation of contaminant concentration.

A typical design of combination probe 10, and in particular its optical chemical sensor 15, can be fabricated according to the device for measuring reflectance and fluorescence of U.S. Pat. No. 5,128,882 and is essentially configured as shown in the cited patent to enable its being pushed deep into a soil sample in the ground for responsive readings. Optical chemical sensor 15 may have an optically transparent window 15a, a light source 15b and a fiber optic link 15c for coupling the induced optical resonances attributed to a particular contaminant in the soil sample to a remote processor 30. Light source 15b may include an appropriately configured end of a fiber 15b' carrying excitation radiation from a remotely located pulsed $N_2$ laser 20b'', for example.

Processor 30 has a spectral analysis unit 31 that can include a detector having an appropriate opto-electronic conversion means for converting the wavelengths of the induced optical resonances to representative signals and may also include at least one appropriate A to D converter 31a, if desired to provide digitized representative chemical sensor signals. From unit 31 the processed signals are fed to an interconnected cathode ray tube (CRT) display unit 32 and a data storage unit 33 via leads 31' and 31'', respectively. From the data storage unit the representative chemical sensor signals selectively may be fed to the CRT display 32 or a printer-plotter 34 in accordance with a computer controlled comparison and correlation or for a visual ensuing comparison and correlation as will be explained below. These constituents and manner of operable interconnection are well known in the art and would be selectable by a routineer from commercially available units to provide at least the functional equivalent of the similar units in the arrangement shown in U.S. Pat. No. 5,128,882.

Combination probe 10, employed in conjunction with the improved method of this invention, additionally incorporates a strain gauge sensor 20. The is fabricated in accordance with well established designs in the penetrometer art and may take the form of at least one strain gauge device. Typically, the probe may be fabricated within the scope of U.S. Pat. No. 3,906,781.

Strain gauge sensor 20 takes strain gauge measurements of tip and sleeve friction on the probe that are attributed to a soil type and condition of the soil sample to produce representative electronic signals representative of an index of soil type to a lead 21 that extends to data storage unit 33 of processor 30.

The data storage unit is provided with an analog to digital converter 33a if it is desired to digitize any incoming signals. The data storage unit may also be the location of a suitable computer that is appropriately coupled to effect a desired switching or transfer of the data and a processing of the data in accordance with a desired data processing procedure. The representative strain gauge sensor signals in the data storage unit may be selectively fed to the CRT display 32 or printer plotter 34 for a computer or visual ensuing comparison and correlation as will be explained below. The soil types which are determined by different ones of the representative strain gauge sensor signals may be sandy soil, silt, clay, etc.

Other environmental influences on contaminant optical response can be gathered in the method of this inventive concept, such as to indicate the parameter of soil moisture condition. Appropriate moisture sensors may be incorporated in the combination probe that yield readings simultaneously and in parallel with chemicals of interest and soil type. An appropriate moisture sensor 25 having a suitable window 25a has an interconnecting data link 25b transmitting data to data storage unit 33 for processing.

The use of strain gauges on an instrumented probe for determining soil types is not new by itself, note the above cited articles by R. S. Olsen and P. K. Robertson. Cone penetrometer systems have used probes instrumented with strain gauges for many years, but prior to this invention the strain gauge probe information was used to determine soil strength characteristics for construction purposes. The method of this invention relies on the use of strain gauge-deduced soil classification as a means of correcting for soil matrix effects on in situ optical chemical measurements. The optical response to a chemical constituent varies by an order of magnitude or more, as a function of soil type. As a consequence, the in situ quantification of a chemical analyte heretofore has been only an order of magnitude estimate at best.

In accordance with this inventive concept, however, soil type and condition are accounted for so that it is possible to improve quantification of optical chemical signals to within a factor of two or better. This improved quantification greatly enhances the capability of using in situ optical chemical sensors as screening tools for mapping out subsurface contaminant plumes. The method addressed herein applies to most if not all in situ measurements of chemical compounds in soils that are presently in use or are contemplated.

This invention is a method for improving the calibration of the response from optical chemical sensors for in situ quantification of chemical constituents in soils. The method relies on using the combination probe instrumented with the strain gauge sensor and moisture sensor to make independent determinations of soil type (or classification) and condition simultaneously in parallel with optical chemical measurements made using the same probe. The soil classification information is used to correct for the effect of differences in the soil matrices on the calibration of the optical response of the chemical sensor. The strain gauge derived soil classification is used as an index to reference different optical chemical response factors determined under controlled laboratory conditions. This determination produces laboratory produced optical chemical response factor signals or predetermined reference signals.

A measurement of the chemicals of interest in accordance with this inventive concept can be the product of a computer implementation by any one of a variety of processing expedients, such as fuzzy (continuous) logic with neural network or other implementations, as referred to below. Optionally, the measurement of the chemicals of interest can be a computer integration, comparison and correlation of the data itself or images created by predetermined reference signals to the optical chemical sensor signals and the strain gauge sensor signals. Another variation is a visual correlation of the predetermined reference signals to the optical chemical sensor signals and the strain gauge sensor signals by a skilled technician who is trained to recognize correlations on CRT display 32 or plotter 34 of the data presented by the predetermined reference signals, optical chemical sensor signals and the strain gauge sensor signals.

In practice this inventive concept includes a determination of optical chemical response factors under controlled laboratory conditions for specific chemical compounds or products added to different soil matrices and conditions (i.e. different soil types, moisture). These laboratory measurements provide predetermined reference signals that are the basis for a series of calibration rules (e.g. If the soil is sandy, response curve slope is high). The use of other in situ sensors such as strain gauge measurements and moisture indications establish soil type and conditions so that parallel in situ optical chemical measurements can be calibrated in terms of the appropriate optical chemical response factor determined. By using, for example, strain gauges to independently determine soil type and conditions at the same location that the optical measurement is made as the combination sensor probe is pushed into the ground, the chemical quantification of the optical signal is greatly improved because effects of the soil matrix and conditions on the optical response can be accounted for. By an integration, using, for instance, fuzzy (continuous) logic with neural network or other implementations, the rules and trends observed in the laboratory, with the actual measurements made in the field, a measurement-specific calibration curve and analyte concentration can be generated.

The approach of this invention interprets measurements in natural systems. It has the potential to dramatically enhance the ability to successfully model natural systems. This invention is compatible with the use of fuzzy logic. Fuzzy logic is severely underutilized in a field for which it seems ideally suited: the interpretation of data collected in natural systems so that its adaptation to expedite this inventive concept is promising. The natural environment, completely removed from the controls of the laboratory or constraints of human-designed systems, represents a maximally fuzzy system: one in which almost all variables are heterogeneous and to some extent unconstrained. The integration of neural networks with fuzzy systems allows this integrated system to learn and respond to a multivariate database, with both Boolean (non-fuzzy) and fuzzy information. Such a system, being massively parallel, allows for much more rapid data processing than does any other, statistically derived interpretation system. Together, these approaches may dramatically enhance the accuracy and efficacy of models of natural systems.

The advantage of the method put forth in this invention is greatly improved quantification of the measured optical response of chemical sensors for in situ measurement of chemical constituents in soils. Prior to this invention optical responses measured in situ with probes pushed into the ground were calibrated in terms of a single optical response factor for a given chemical constituent. The prior art calibration method did not take into account the fact that optical response for a specific chemical compound or product could vary by an order of magnitude or more depending on the soil type (e.g. sand, silt, clay, etc.) or condition, see S. E. Apitz, L. M. Borbridge, G. A. Theriault and S. H. Lieberman, "Remote in situ Determination of Fuel Products in Soils: Field Results and Laboratory Investigations," *Analusis*, vol. 20, pp. 461-474 (invited paper), (1992); and S. E. Apitz, L. M. Borbridge, K. Bracchi and S. H. Lieberman, "The Fluorescent Response of Fuels in Soils: Insights into Fuel-Soil Interactions," in *International Symposium on Environmental Sensing, EOS/SPIE Proceedings, vol.* 1716 (in press), (1992); and S. E. Apitz, G. A. Theriault and S. H. Lieberman, "Optimization of the Optical Characteristics of a Fiber-optic Guided Fluorescence Technique for the in situ Evaluation of Fuels in Soils," in *SPIE Proceedings Vol.* 1637, *Environmental Process and Treatment Technologies*, T. Vo-Dinh, ed., pp. 241-254 (1992). An advantage of this inventive concept is the use of soil classification information derived from strain gauge measurements of tip and sleeve friction on the probe to provide an index of soil type so that the appropriate optical response factor can be used for calibration of the optical chemical sensor. Other sensors exist for taking into account environmental effects on sensor performance, but none for taking into account environmental controls on the response of the contaminant being sensed.

While one aspect of this inventive concept has been concerned with the integration of CPT-generated soil class into calibration algorithms, it is within the scope of other aspects of this inventive concept to gather data from other sources of soil class and characteristics, such as manual probes, separate optical measurements, or stratigraphic records to be integrated into algorithms for improved results. Also, concurrent measurements of environmental conditions such as moisture content, temperature, oxygen content, and mineralogy can all be integrated. Once the effects of these conditions on in situ optical response have been characterized, any measurable parameter can be integrated into the quantitative algorithms. Similar soil class dependent calibration algorithms will have to be developed and taken into account for any in situ optical determination of contaminants or naturally occurring compounds in soils.

Substrate-dependent calibration algorithms can also be used for in situ optical chemical measurements in substrates other than soils. They can be applied to marine sediments, for the purpose of in situ evaluation of contaminants and naturally occurring substances in marine sediment layers. Furthermore, they can be applied to any in situ optical measurement of a substance on a solid matrix.

Optical determination of analyte concentration enhanced by soil class measurements has many applications pertinent to the fiber optic sensor equipped cone, penetrometer system for subsurface screening of hazardous waste sites. The fiber optic chemical sensor provides continuous depth profiles of in situ fluorescence in parallel with a profile of soil class and strength characteristics. These soil classes will be taken into account in calibration algorithms if they are needed to provide a responsive indication.

Referring now to FIG. 2, an exemplary process 50 in accordance with this inventive concept is depicted. This process assures the quantitative assessment of chemicals of interest by a parallel probe having a chemical sensor device 15 and a strain gauge device 20 and for providing representative chemical sensor signals and strain gauge signals. As a prerequisite for the process to assure the quantitative assessment, a determining 55 of chemical response factor signals is made under laboratory conditions for different soil matrices to provide predetermined optical chemical response factor reference signals. In other words, known concentrations of particular chemicals of interest in different known soil types are measured with a chemical sensing device that is identical or the same as or substantially the same as that disclosed herein and the predetermined reference signals therefrom are provided via an input 55a to the data storage unit of processor 30. The chemical response factor signals are digitized, if desired, and appropriately stored in the data storage unit for selective utilization in accordance with this inventive concept at the display 32 or printer plotter 34. An inserting 60 of probe 10 which contains chemical sensor 20 and strain gauge 15, and, optionally, moisture sensor 25, in a test soil sample is performed by various penetrometer expedients. The penetration can be anywhere from a few inches to many feet, i.e. in excess of 100, so that the chemical sensors and strain gauge are appropriately placed in the desired soil sample to take the desired readings.

With the probe inserted in place, a producing 65 of the parallel representative chemical sensor signals and strain gauge signals progresses in accordance with well established techniques in the art so that a feeding 70 of the parallel chemical sensor signals and strain gauge signals can be made to processor 30. In the processor, the strain gauge signals and chemical sensor signals are appropriately processed to include a comparing 75 of the chemical sensor signals and the strain gauge signals to the predetermined optical chemical response factor reference signals in the processor to provide in situ quantification of chemicals of interest in the soil sample. The comparing may be performed by a variety of methods. One of the most apparent is a simple display of the chemical sensor signals and strain gauge signals on CRT display 32 and a simultaneous or sequential display of the predetermined reference signals 55a on the CRT display to allow a skilled scientist or technician to make a correlation and quantitative assessment. Optionally, the predetermined reference signals, the chemical sensor signals and the strain gauge signals could be printed out by printer-plotter 34 to allow a more detailed study and correlation of the results to enable a finding of the concentrations of chemicals of interest. A host of signal comparison-integration-correlation procedures for appropriate processing of the predetermined reference signals, chemical sensor signals and strain gauge signals can be selected in accordance with techniques and procedures well known to those skilled in the data processing art to affect the in situ quantitative assessment by analyzer 30.

Obviously, many modifications and variations of the present invention are possible in the light of the above teachings. It is therefore to be understood that within the scope of the appended claims, the invention may be practiced otherwise than as specifically described.

I claim:
1. A method for the in situ quantification of chemicals of interest in a soil sample by optical methods comprising:
   determining optical chemical response factors for chemicals of interest which are added in known amounts to discrete soil matrices (types) and conditions (moisture content, for example) under controlled laboratory conditions to provide predetermined optical chemical response factor reference signals;
   coupling said predetermined optical chemical response factor reference signals to a processor having the capability to store said predetermined optical chemical response factor reference signals therein;
   providing a combination probe having an optical chemical sensor having the capability to produce chemical sensor signals representative of a chemical of interest in said soil sample and further having a strain gauge sensor having the capability to produce strain gauge signals representative of soil type of said soil sample;
   inserting said combination probe into said soil sample;
   producing said chemical sensor signals in said optical chemical sensor and said strain gauge signals in said strain gauge sensor, simultaneously and in parallel;
   transmitting said chemical sensor signals and said strain gauge signals to said processor; and
   correlating said chemical sensor signals and said strain gauge signals with said predetermined optical chemical response factor reference signals in said processor to provide said in situ quantification of said chemicals of interest in said soil sample, said correlating involving the use of said strain gauge signals representative of said soil type of said soil sample to select a chemical response factor from said predetermined optical chemical response factor reference signals, said chemical response factor being indicative of a chemical of interest in a particular soil type of said soil sample, to provide said in situ quantification of said chemicals of interest from said chemical sensor signals of said soil sample.

2. The method according to claim 1 in which the step of said providing includes a further providing of a moisture sensor in said combination probe having the capability to produce moisture condition signals representative of soil moisture content of said soil sample, the step of said inserting further includes the inserting of said moisture sensor in said soil sample, the step of said producing further includes the producing of said moisture condition signals simultaneously and in parallel, with said chemical sensor signals and said strain gauge signals, the step of said transmitting further includes the transmitting of said moisture condition signals to said processor and the step of said correlating includes the correlating of said moisture condition signals with said predetermined optical chemical response factor reference signals in said processor, said chemical response factor being further indicative of a particular moisture content of said soil sample.

* * * * *